(12) United States Patent
Snow

(10) Patent No.: US 8,901,232 B2
(45) Date of Patent: Dec. 2, 2014

(54) POLYMERS FOR SURGEONS GLOVES

(75) Inventor: George E. Snow, Medina, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 13/885,055

(22) PCT Filed: Nov. 15, 2011

(86) PCT No.: PCT/US2011/060719
§ 371 (c)(1),
(2), (4) Date: May 13, 2013

(87) PCT Pub. No.: WO2012/068059
PCT Pub. Date: May 24, 2012

(65) Prior Publication Data
US 2013/0225755 A1     Aug. 29, 2013

Related U.S. Application Data

(60) Provisional application No. 61/414,954, filed on Nov. 18, 2010.

(51) Int. Cl.
| | | |
|---|---|---|
| *C08L 75/00* | (2006.01) |
| *C08G 18/08* | (2006.01) |
| *C08L 75/04* | (2006.01) |
| *C08G 18/12* | (2006.01) |
| *C08G 18/34* | (2006.01) |
| *C08G 18/48* | (2006.01) |
| *C08G 18/66* | (2006.01) |
| *C08G 18/76* | (2006.01) |
| *A61L 31/04* | (2006.01) |
| *B29C 41/00* | (2006.01) |
| *C08L 33/06* | (2006.01) |
| *C08L 33/08* | (2006.01) |

(52) U.S. Cl.
CPC ............. *C08L 75/04* (2013.01); *C08G 18/0823* (2013.01); *C08G 18/12* (2013.01); *C08G 18/348* (2013.01); *C08G 18/4854* (2013.01); *C08G 18/6692* (2013.01); *C08G 18/7621* (2013.01); *A61L 31/04* (2013.01); *B29C 41/003* (2013.01); *C08L 33/06* (2013.01); *C08L 33/08* (2013.01)
USPC .......................................... 524/507; 524/591

(58) Field of Classification Search
USPC ......................................................... 524/507
See application file for complete search history.

(56) References Cited

U.S. PATENT DOCUMENTS

| | | | | |
|---|---|---|---|---|
| 5,997,969 | A * | 12/1999 | Gardon .................... | 428/35.7 |
| 6,017,997 | A * | 1/2000 | Snow et al. ................. | 524/591 |
| 7,045,573 | B2 * | 5/2006 | Mayer et al. ................. | 524/840 |
| 2009/0288237 | A1 | 11/2009 | Chen | |

FOREIGN PATENT DOCUMENTS

WO     2004074341 A1     9/2004

* cited by examiner

*Primary Examiner* — Hui Chin
(74) *Attorney, Agent, or Firm* — Samuel B. Laferty

(57) ABSTRACT

This invention relates to aqueous polyurethane compositions suitable for dipped surgeon's gloves and related articles needing toughness, pliability, and some solvent resistance. The gloves replace natural latex gloves which can cause allergic reactions and/or isoprene gloves which have their own drawbacks.

19 Claims, No Drawings

POLYMERS FOR SURGEONS GLOVES

FIELD OF INVENTION

This application relates to polyurethane dispersions in water that form tough low modulus films, desirable to form dipped rubbery articles, such as gloves and related medical/personal care protective goods.

BACKGROUND OF THE INVENTION

U.S. Pat. No. 5,997,969 discloses a polyurethane glove.

U.S. Pat. No. 6,017,997 discloses waterborne polyurethane having film properties comparable to rubber.

U.S. Pat. No. 7,045,573 discloses polyurethane dispersions (PUD) with improved isopropanol resistance, flexibility and softness.

US 2009/0288237A1 discloses a flexible glove and the preparation method thereof.

SUMMARY OF THE INVENTION

This invention discloses a polymer with improved properties for dip formed goods, such as surgeon's gloves. The urethane portion of the polymer has enhanced toughness to resist tearing, lower modulus to enhance comfort and grip, and alcohol resistance so that sterilizing solutions can be used without compromising glove integrity. An optional acrylate polymer can be blended with the urethane polymer dispersion or formed within the urethane polymer dispersion (typically referred to as hybrid polyurethane) to enhance alcohol resistance. Crosslinkers can be included with the polymer(s) or added during dipping or post-dipping to enhance crosslink density and ultimately tensile strength and tear resistance.

DETAILED DESCRIPTION OF THE INVENTION

An aqueous polyurethane dispersion is described that comprises a urethane polymer dispersed in an aqueous phase. The dispersion optionally includes an acrylate polymer (dispersed in water or incorporated into the urethane phase) to enhance the resistance to alcohol, often used for sterilization. The polyurethane differs from other polyurethanes in its high tensile strength in combination with relatively low modulus at 100% and 500% elongation. These physical properties are associated with a large amount of relatively high molecular weight polyol having a relatively soft nature being included in the polyurethane. Crosslinking can help the tensile strength but too much crosslinking can negatively affect the low modulus at 100% and 500% elongation. A relatively low amount of anionic (e.g., carboxylic acid and the like) content in the polyurethane is desirable. Polyethers, polycarbonates, and polydienes provide more hydrolytic stability of the polymer chains than is achieved with polyesters.

In addition, "polyurethane" is a generic term used to describe polymers including oligomers (e.g., prepolymers) which contain the urethane group, i.e., —O—C(=O)—NH—, regardless of how they are made. As well known, these polyurethanes can contain additional groups such as urea, allophanate, biuret, carbodiimide, oxazolidinyl, isocynaurate, uretdione, alcohol, amine, hydrazide, siloxane, silane, ketone, olefin, etc., in addition to urethane groups.

"Wt. %" means the number of parts by weight of monomer per 100 parts by weight of polymer, or the number of parts by weight of ingredient per 100 parts by weight of composition or material of which the ingredient forms a part.

"Aqueous medium" means a composition containing a substantial amount of water, e.g., at least 50 or 75 wt. % water based on the aqueous medium of the dispersion. It may contain other ingredients as well.

The "final polyurethane product" refers to the form of the polyurethane in the aqueous dispersion product of this invention. Where the polyurethane prepolymer is optionally chain extended, the final polyurethane product is this chain extended polymer. Where the polyurethane prepolymer is not chain extended, the final polyurethane product is the prepolymer itself.

"Substantial absence of water" refers to compositions formed without the intentional addition of any significant amount water, e.g., about 2 wt. % or less or so.

"Substantial absence of surfactant" as well as "substantially free of residual surfactant" in reference to a dispersion, means that the dispersion is made without intentionally including a surfactant.

Waterborne Polyurethanes

This invention, in one embodiment, relates to polyurethanes which are derived from aqueous dispersions and which, when dried and cured, produce solid polyurethane products with high elongation to break, high tensile strength, e.g., >2500 psi (17.2 MPa), and low modulus at 100 and 500% elongation, e.g., <290 psi (2.0 MPa) and <700 psi (4.8 MPa), respectively.

Polyurethanes are normally made by reacting together three principle ingredients, multi-functional isocyanate-reactive compound (also known as a macroglycol), a diisocyanate, and an optional chain extender, such as, short-chain di- and polyols, di- and polyamines or the like. Polyurethanes in which the multi-functional isocyanate-reactive compound is a polyether, a hydrocarbon, or a polycarbonate exhibit superior resistance against degradation by hydrolysis than when the multi-functional isocyanate-reactive compound is a polyester.

Polyurethanes are available in the form of aqueous dispersions to make dipped articles and coatings. In these, it is customary to include in the backbone of the polymer, at least one "water-dispersibility enhancing compound" (i.e., a comonomer) which helps disperse the polymer in the aqueous medium by reducing interfacial tension and stabilizing the dispersed phase against aggregation. Dimethylolpropanoic acid is normally used for this purpose, although other analogous compounds can be used.

Such waterborne polyurethanes are well known and described, for example, in U.S. Pat. No. 6,576,702, the entire disclosure of which is incorporated herein by reference. They may be prepared by reacting (1) at least one polyisocyanate; (2) at least one multi-functional isocyanate-reactive compound; and (3) at least one water-dispersibility enhancing compound to form an isocyanate terminated prepolymer, which can then be optionally neutralized by reaction with (4) at least one neutralizing agent (e.g., triethylamine), and then dispersed in (5) water to form an aqueous prepolymer dispersion. Such dispersions can be used, as is, to form tough, transparent coatings and other products. Alternatively, such dispersions can be treated by chain extending the dispersed prepolymer to form more complex polyurethanes, for example, by reaction with (6) water or (7) an amine having two or more primary and/or secondary amine groups. The poly(urethane-urea)s so formed can then be used to form tough, transparent coatings and other products.

Essentially, any ingredient that has previously been used, or which may be used in the future to make waterborne polyurethanes, can be used to make the waterborne polyurethane polymers and prepolymers of this invention, provided the components do not degrade the tensile strength, increase the modulus values, or degrade the ethanol resistance. Examples include the following:

(i) Polyisocyanate

Suitable polyisocyanates have an average of about two or more isocyanate groups, preferably an average of about two to about four isocyanate groups per molecule and include aliphatic, cycloaliphatic, araliphatic, aromatic, and heterocyclic polyisocyanates, as well as products of their oligomerization, used alone or in mixtures of two or more. Diisocyanates are more preferred.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, and the like. Polyisocyanates, having fewer than 5 carbon atoms, can be used but are less preferred because of their high volatility and toxicity. Preferred aliphatic polyisocyanates include hexamethylene-1,6-diisocyanate, 2,2,4-trimethyl-hexamethylenediisocyanate, and 2,4,4-trimethyl-hexamethylene diisocyanate.

Specific examples of suitable cycloaliphatic polyisocyanates include dicyclohexylmethane diisocyanate, (commercially available as Desmodur™ W from Bayer Corporation), isophorone diisocyanate, 1,4-cyclohexane diisocyanate, 1,3-bis-(isocyanatomethyl) cyclohexane, and the like. Preferred cycloaliphatic polyisocyanates include dicyclohexylmethane diisocyanate and isophorone diisocyanate.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate.

Examples of suitable aromatic polyisocyanates include 4,4'-diphenylmethylene diisocyanate (MDI), toluene diisocyanate (TDI), their isomers, naphthalene diisocyanate, and the like. Preferred aromatic polyisocyanates include 4,4'-diphenylmethylene diisocyanate and toluene diisocyanate.

Examples of suitable heterocyclic isocyanates include 5,5'-methylenebisfurfuryl isocyanate and 5,5'-isopropylidenebisfurfuryl isocyanate.

In one embodiment, the isocyanate component has an average functionality between about 1.9 and about 2.1, more desirably between about 1.95 and about 2.05. In one embodiment, desirably at least 80 wt. % of the isocyanate component is a diisocyanate (leaving an opportunity for a few monofunctional and trifunctional species) and in a preferred embodiment at least about 90 wt. %. In one embodiment, desirably at least 50 or 80 wt. % of the isocyanate component is an aromatic isocyanate and more desirably at least 90 wt. %. The limitations on wt. % difunctional and wt. % aromatic are desirably combined in one embodiment.

As the molecular weight of the multi-functional isocyanate-reactive compound increases, the amount (in wt. %) of the isocyanate component decreases, other factors being held constant. The isocyanate component contributes to the hardness and modulus of the polyurethane. In one embodiment, desirably a high molecular weight multi-functional isocyanate-reactive compound is used in a large amount, such that the amount of isocyanate component in the polyurethane is less than 20 wt. % of the polyurethane, more desirably less than 18 wt. %, still more desirably less than 15, less than 13, and preferably less than 11 wt. %.

(ii) Multi-Functional Isocyanate-Reactive Compound

Any compound that includes: (1) having at least two functional groups, each of which is capable of reacting with an isocyanate group to form a urethane linkage, as well as (2) ether or polycarbonate linkages between at least two of these functional groups (a polyether or polycarbonate multi-functional isocyanate-reactive compound) can be used as the multi-functional isocyanate-reactive compound to make the inventive waterborne polyurethanes of this invention.

The multi-functional isocyanate-reactive compound contributes to the tensile strength and if it is a soft polymer of higher molecular weight contributes to low modulus at 100% and 500% elongation of the polyurethane. In one embodiment, desirably a high molecular weight (e.g., Mn greater than 1500 g/mole and more desirably greater than 2000 g/mole) multi-functional isocyanate-reactive compound is used in a large amount, such that the amount of multi-functional isocyanate-reactive compound in the polyurethane is greater than 80 wt. % of the polyurethane, more desirably greater than 82 wt. %, still more desirably greater than 84, greater than 85, and preferably greater than 86 wt. %. In one embodiment, desirably at least 80, 82, 84, 85 or 86 wt. % of the high molecular weight multi-functional isocyanate-reactive compound is a polyether from alkylene oxide of 3 to 6 carbon atoms such as propylene oxide or butylene oxide or a polycarbonate as described later or mixtures thereof. In one embodiment, at least 80, 82, 84, 85 or 86 wt. % of the polyurethane is said polyether or said polycarbonate. This limitation may be combined with the above limitations. Preferred polyethers include polypropylene glycol) and, polytetrahydrofuran.

The multi-functional isocyanate-reactive compound may include a small percentage of ester linkages between these at least two functional groups, but polymers with ester linkages are less preferred in this particular invention. The most common ester-containing multi-functional isocyanate-reactive compound is the polyester polyols including alkyds and esters of phosphonic acid.

The diols, used in making these polyester polyols, include alkylene glycols, e.g., ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcycohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, hydroxylated bisphenols, polyether glycols, halogenated diols, and the like, and mixtures thereof. Preferred diols include ethylene glycol, diethylene glycol, butylene glycol, hexane diol, and neopentyl glycol.

Suitable carboxylic acids, used in making these polyester polyols, include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as dimeric oleic acid, and the like, and mixtures thereof. Preferred polycarboxylic acids, used in making the polyester polyols, include aliphatic or aromatic dibasic acids.

Preferred polyethers include poly(propylene glycol) and, polytetrahydrofuran.

Polycarbonate polyols can also be used as the multi-functional isocyanate-reactive compound of this invention. Such compounds also include the —O—C(=O)—O— group.

They can be obtained, for example, from the reaction of (A) diols such 1,3-propanediol, 1,4-butanediol, 1,6-hexanediol, diethylene glycol, triethylene glycol, tetraethylene glycol, and the like, and mixtures thereof with (B) diarylcarbonates such as diphenylcarbonate or phosgene. Aliphatic and cycloaliphatic polycarbonate polyols can also be used.

The multi-functional isocyanate-reactive compound (e.g., macroglycol) used to make the waterborne polyurethane of this invention will normally be polymeric and hence will have a molecular weight of at least about 500 Daltons, more typically about 1,000-10,000 Daltons, or even 1,000-6,000 Daltons. While the term multi-functional isocyanate-reactive compound is used, it is understood that these multi-functional isocyanate-reactive compounds can have two or more hydroxyl groups (or other isocyanate reactive groups) per molecule (i.e., the multi-functional isocyanate-reactive compound is not limited to only two isocyanate reactive groups). Low molecular weight versions of these compounds can also be used, i.e., compounds having a number average molecular weight less than about 500 Dalton such as aliphatic, cycloaliphatic and aromatic polyols, especially diols although most authors label the lower molecular weight glycol species (e.g., less than 500 Daltons molecular weight) as chain extenders.

Included in this group of comonomers are the low molecular weight compounds typically referred to as "chain extenders". Examples include low molecular weight polyols with number-average molecular weight less than about 500 Daltons and diols, diamines and polyamines described above. "Polyol" in this context means any product having an average of about two or more hydroxyl groups per molecule. Specific examples include aliphatic, cycloaliphatic and aromatic polyols, especially diols, having 2-20 carbon atoms, more typically 2-10 carbon atoms, such as 1,4-butanediol. Any other compounds known to function as chain extenders in polyester polyols can also be used.

(iv) Water-Dispersibility Enhancing Compounds

Polyurethanes are generally hydrophobic and not water-dispersible. Therefore, at least one water-dispersibility enhancing compound (i.e., monomer), which has at least one, hydrophilic, ionic or potentially ionic group is optionally included in the polyurethane polymers and prepolymers of this invention to assist dispersion of the polymer/prepolymer in water. Typically, this is done by incorporating a compound bearing at least one hydrophilic group or a group that can be made hydrophilic (e.g., by chemical modifications such as neutralization) into the polymer/prepolymer chain. These compounds may be of a nonionic, anionic, cationic or zwitterionic nature or the combination thereof. For example, anionic groups and their salts such as carboxylic acid groups, sulfonate groups, and/or phosphonate groups can be incorporated into the prepolymer in an inactive form, and subsequently activated by a salt-forming compound, such as a tertiary amine, or other basic compound. It is recognized that sulfonate and phosphonate (and possibly others) groups can also stabilize a dispersion of the inventive polyurethane. In the preferred embodiment of the invention, the prepolymer will have a carboxylic acid content (just the COOH portion of the repeat unit, having a molecular weight of 45 g/mole) of less than 1 wt. %, based on the weight of the polyurethane).

In terms of acid number, this is less than about 12.6 mg KOH/gram, and more desirably less than 0.75 wt. % (about 8.8 mg KOH/g). Other water-dispersibility enhancing compounds can also be reacted into the prepolymer backbone through urethane linkages or urea linkages, including lateral or terminal hydrophilic ethylene oxide or ureido units. In one embodiment, desirably any terminal hydrophilic poly(ethylene oxide) or polymers containing ethylene oxide based repeat units are present in an amount of less than 2 wt. %, more desirably less than 1 wt. % based on the weight of the polyurethane.

Water dispersibility enhancing compounds of the ionic type of particular interest are those which can incorporate carboxyl groups into the prepolymer. Normally, they are derived from hydroxy-carboxylic acids having the general formula $(HO)_xQ(COOH)_y$, wherein Q is a straight or branched hydrocarbon radical containing 1 to 12 carbon atoms, and x and y are 1 to 3. Examples of such hydroxy-carboxylic acids include dimethylolpropanoic acid (DMPA), dimethylol butanoic acid (DMBA), citric acid, tartaric acid, glycolic acid, lactic acid, malic acid, dihydroxymalic acid, dihydroxytartaric acid, and the like, and mixtures thereof. Dihydroxy-carboxylic acids are more preferred with dimethylolpropanoic acid (DMPA) and dimethylol butanoic acid (DMBA) being most preferred.

Another group of water-dispersibility enhancing compounds of the nonionic type of particular interest are side chain hydrophilic monomers. Some examples include alkylene oxide polymers and copolymers in which the alkylene oxide groups have from 2-10 carbon atoms as shown, for example, in U.S. Pat. No. 6,897,281, the disclosure of which is incorporated herein by reference.

Chain Extenders for Dispersion

The aqueous prepolymer composite particle dispersions, produced as described above, can be used as is, if desired. Alternatively, they can be chain extended to convert the prepolymers in the composite particles to more complex polyurethanes such as poly(urethane-urea)s.

As a chain extender, at least one of water, inorganic or organic polyamine having an average of about 2 or more primary and/or secondary amine groups, polyalcohols, or combinations thereof, is suitable for use in this invention. Suitable organic amines, for use as a chain extender, include amines listed above and also diethylene triamine (DETA), ethylene diamine (EDA), meta-xylylenediamine (MXDA), aminoethyl ethanolamine (AEEA), 2-methyl pentane diamine (Dytek A), and the like, and mixtures thereof. Also, suitable for practice in this invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, sulfonated primary and/or secondary amines, and the like, and mixtures thereof. Suitable inorganic amines include hydrazine, substituted hydrazines, and hydrazine reaction products, and the like, and mixtures thereof. Suitable polyalcohols include those having from 2 to 12 carbon atoms, preferably from 2 to 8 carbon atoms, such as ethylene glycol, diethylene glycol, neopentyl glycol, butanediols, hexanediol, and the like, and mixtures thereof. Suitable ureas include urea and it derivatives, and the like, and mixtures thereof. Hydrazine and/or Dytek A are preferred and is most preferably used as a solution in water. The amount of chain extender typically ranges from about 0.5 to about 1.1 equivalents based on available isocyanate.

(iv) Compounds Having at Least One Crosslinkable Functional Group

Compounds having at least one crosslinkable functional group or site can also be incorporated into the polyurethane prepolymers of the present invention, if desired. Examples of these optional compounds or sites include those having carboxylic, carbonyl, amine, hydroxyl, epoxy, acetoacetoxy, olefinic and hydrazide groups, blocked isocyanates, and the like, and mixtures of such groups and the same groups, in protected forms, which can be reversed back into original groups from which they were derived.

Other suitable compounds providing crosslinking sites include thioglycolic acid, 2,6-dihydroxybenzoic acid, and the like, and mixtures thereof.

(v) Catalysts

The prepolymer may be formed without the use of a catalyst, if desired, but catalyst may be preferred in some instances. Examples of suitable catalysts to promote the formation of urethane linkage from the reaction of an isocyanate group with a hydroxyl group include stannous octoate (T9), dibutyl tin dilaurate, and tertiary amine compounds, such as triethylamine and bis-(dimethylaminoethyl) ether, morpholine compounds such as beta,beta-dimorpholinodiethyl ether, bismuth carboxylates, zinc bismuth carboxylates, iron (III) chloride, potassium octoate, potassium acetate and zirconium catalysts K-KAT® XC-9213 and K-KAT® 6212 from King Industries.

Some amine catalysts can be permanently incorporated into the backbone of polyurethane. These include N-methyl diethanolamine, N-ethyl diethanolamine, methicol, N,N-Bis (2-hydroxyethyl)isonicotinamide (BIN), JEFFCAT® DPA, JEFFCAT® ZF-10, JEFFCAT® ZR-50, JEFFCAT® Z-110 from Huntsman, and the like.

The preferred catalysts are DABCO® (diazabicyclo[2.2.2] octane), from Air Products, a mixture of 2-ethylhexanoic acid and stannous octoate, e.g., FASCAT® 2003 from Elf Atochem North America., JEFFCAT® DPA from Huntsman, and K-KAT XC-9213 from King Industries.

The amount of catalyst used to form the prepolymer, if used at all, will typically be from about 5 to about 200 parts per million of the total weight of prepolymer reactants.

(vi) Isocyanate Blocking Agents

Several types of compounds can be employed as blocking (a.k.a., protecting or masking) agents. Their function is to temporarily protect isocyanate groups from undesired reactions. The main requirement for the blocking compound is for its reaction with isocyanate to be reversible. When the reaction is reversed, the isocyanate group is regenerated and is available for further reactions. The reverse reaction can be triggered by physical or chemical means, for example, by elevated temperatures, radiation, vacuum, catalysts, compounds with active hydrogen, or combinations thereof Examples of blocking agents include oximes, phenols, alcohols, lactams, imidazoles, pyrazoles, acids, mercaptans, imides, secondary amines, sulfites, acetoacetates and derivatives of malonic acid.

Oximes are generally preferred but can be replaced partially or in full by other blocking agents. Oximes can be represented by a general formula CRR'=NOH, where R and R' may independently be H or $C_nH_{2n+1}$. R and R' may also contain cycloaliphatic, aromatic groups, and groups with heteroatoms including heterocyclic groups. The oxime may be an aldoxime when one or both R and R' are hydrogen, or ketoxime when both R and R' are hydrocarbyl groups. Examples of aldoximes include formaldoxime, acetaldoxime, propionaldoxime, butyraldoxime, benzaldoxime and the like. Examples of ketoximes include acetoxime, butanone oxime, cyclohexanone oxime, acetophenone oxime and the like.

Other preferred blocking agents include lactams, secondary and tertiary alcohols, pyrazoles and their mixtures. Some specific examples of other suitable blocking agents include dimethyl malonate, triazole, caprolactam, phenol, dimethylpyrazole, dibutylamine, diisopropylamine, tert-butanol, cyclohexanol, and isopropanol. Combinations of two or more blocking agents can be used if a stepwise reaction is desired, particularly mixtures of blocking agents which deblock at different temperatures.

The deblocking may occur during chain extension or during polymer drying and/or curing. Often it is preferred to use a blocking agent, which will evaporate from the polymer during drying or curing. In these cases, low molecular weight oximes such as acetoxime, butanone oxime, butyraldoxime and the like are preferred.

(vii) Ingredient Proportions

Normally, the prepolymer produced by the present invention will be isocyanate-terminated. For this purpose, the ratio of polyisocyanate to multi-functional isocyanate-reactive compound in the prepolymer typically ranges from about 1.05/1 to about 1.5/1 and preferably from about 1.1/1 to about 1.4/1. In this context, "equivalent basis" means the total number of reactive isocyanate moieties of the polyisocyanate versus the total number of isocyanate-reactive moieties of the multi-functional isocyanate-reactive compound or compounds. In other cases, a prepolymer can be produced with all isocyanate groups reacted away. In this case, a stoichiometric excess of isocyanate-reactive compounds over isocyanates is used.

In many embodiments of this invention, the multi-functional isocyanate-reactive compound component will be composed entirely of one or more polyether (e.g., polypropylene oxide or polybutylene oxide) or polycarbonate containing multi-functional isocyanate-reactive compounds, as described above. In other embodiments, ≤30%, ≤20%, ≤10 or even ≤5% of the multi-functional isocyanate-reactive compound component on an equivalent basis can be composed of one or more ester multi-functional isocyanate-reactive compounds. Embodiments in which ≥70%, ≥80%, ≥90%, and even ≥95%, of the multi-functional isocyanate-reactive compound component basis are polyethers or polycarbonates, as described above, are preferred.

The amount of optional compounds having crosslinkable functional groups in the prepolymer will typically be up to about 1 milliequivalent, preferably from about 0.05 to about 0.5 milliequivalent, and more preferably from about 0.1 to about 0.3 milliequivalent per gram of final polyurethane on a dry weight basis.

Crosslinkers for the urethane polymer can include aziridines (Xama®-7), isocyanates, melamines (e.g., Cymel™), carbodiimides (e.g., Carbodilite™ E-02), epoxides, polyvalent metal ions (Zn, Zr, Ca, Al), and epoxysilanes. The above crosslinkers can be used in amounts from 0.2 or 0.5 to about 2 or 5 wt. % of the polyurethane weight. Crosslinkers, that do not generate formaldehyde as part of the crosslinking reaction, are preferred. They can, optionally, be added as appropriate before and/or during the processing of the dispersions of this invention into finished products, as is well known to those skilled in the art.

Forming the Aqueous Dispersion

The polyurethane prepolymer of this invention is formed in a conventional way, such as by combining the above ingredients together and allowing them to react for a suitable period of time, normally with suitable mixing. Thereafter, the prepolymer so formed, which is usually in the form of a syrupy liquid, can then be converted into an aqueous dispersion in conventional way such as by combining the prepolymer with water with suitable mixing, for example. Where solvent polymerization is employed, the solvent (e.g., acetone and/or MEK) and other volatile components can optionally be distilled off from the final dispersion, if desired.

Before continuing with discussion of the preferred process, it is noted that other processes and combination of processes can also be used to manufacture the polyurethane dispersions of the present invention, including but not limited to the following:

1. Dispersing prepolymer by shear forces with emulsifiers (external emulsifiers, such as surfactants, or internal emulsifiers having anionic and/or cationic groups as part of or pendant to the polyurethane backbone, and/or as end groups on the polyurethane backbone).
2. Acetone/MEK process. (preferred) A prepolymer is formed with or without the presence of acetone, MEK ($CH_3C(O)CH_2CH_3$.), and/or other polar solvents such as ethanol, 1-propanol, 2-propanol, or butanol that are non-reactive and easily distilled. The prepolymer is further diluted in said solvents as necessary, and chain extended with an active hydrogen-containing compound. Water is added to the chain-extended polyurethane, and the solvents are distilled off. A variation on this process would be to chain extend the prepolymer after its dispersion into water.
3. Melt dispersion process. An isocyanate-terminated prepolymer is formed, and then reacted with an excess of ammonia or urea to form a low molecular weight oligomer having terminal urea or biuret groups. This oligomer is dispersed in water and chain extended by methylolation of the biuret groups with formaldehyde.
4. Ketazine and ketimine processes. Hydrazines or diamines are reacted with ketones to form ketazines or ketimines. These are added to a prepolymer, and remain inert to the isocyanate. As the prepolymer is dispersed in water, the hydrazine or diamine is liberated, and chain extension takes place as the dispersion is taking place.
5. Continuous process polymerization. An isocyanate-terminated prepolymer is formed. This prepolymer is pumped through high shear mixing head(s) and dispersed into water and then chain extended at said mixing head(s), or dispersed and chain extended simultaneously at said mixing head(s). This is accomplished by multiple streams consisting of prepolymer (or neutralized prepolymer), optional neutralizing agent, water, and optional chain extender and/or surfactant.
6. Reverse feed process. Water and optional neutralizing agent(s) and/or extender amine(s) are charged to the prepolymer under agitation. The prepolymer can be neutralized before water and/or diamine chain extender are added.

In one embodiment of the invention, where the prepolymer includes enough water-dispersibility enhancing compound to form a stable dispersion without added emulsifiers (surfactants), the dispersion can be made without such compounds, i.e., substantially free of surfactants, if desired. The advantage of this approach is that the coatings or other products made from the polyurethane exhibit less water sensitivity, better film formation, less foaming and reduced growth of mold, bacteria and so forth.

In those instances in which the prepolymer includes water-dispersibility enhancing compounds with pendant carboxyl groups, these carboxyl groups can be neutralized by converting them to carboxylate anions for enhancing the water-dispersibility of the prepolymer.

Suitable neutralizing agents, for this purpose, include tertiary amines, metal hydroxides, ammonium hydroxide, phosphines, and other agents well known to those skilled in the art. Tertiary amines and ammonium hydroxide are preferred, such as triethyl amine (TEA), dimethyl ethanolamine (DMEA), N-methyl morpholine, and the like, and mixtures thereof. It is recognized that primary or secondary amines may be used in place of tertiary amines, if they are sufficiently hindered to avoid interfering with the chain extension process.

The aqueous polyurethane prepolymer dispersions, obtained in the manner described above, whether or not neutralized, can be used, as is, to provide dipping solutions, coatings, films and other solid polyurethane products. Additionally or alternatively, these dispersions can be treated in a conventional way to chain extend the prepolymers therein to form poly(urethane-urea)s. For this purpose, water, inorganic and/or organic polyamines having two or more primary and/or secondary amine groups, polyalcohols, or combinations thereof, can be used. Suitable organic amines for use as a chain extender include diethylene triamine (DETA), ethylene diamine (EDA), meta-xylylenediamine (MXDA), aminoethyl ethanolamine (AEEA), 2-methylpentane-1,5-diamine (e.g., Dytek™A), and the like, and mixtures thereof. Also suitable for practice in this invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, sulfonated primary and/or secondary amines, and the like, and mixtures thereof. Suitable inorganic amines include hydrazine, substituted hydrazines, and hydrazine reaction products, and the like, and mixtures thereof. Suitable polyalcohols include those having from 2 to 12 carbon atoms, preferably from 2 to 8 carbon atoms, such as ethylene glycol, diethylene glycol, neopentyl glycol, butanediols, hexanediol, and the like, and mixtures thereof.

The aqueous polyurethane dispersions obtained in this way can also be used, "as is", to provide coatings, films, dipped articles, and other solid polyurethane products.

(iv) Other Additives for Preparation of Dispersions

Other additives, well known to those skilled in the art, can be used to aid in preparation of the dispersions of this invention. Such additives include defoamers, antioxidants such as hindered phenols and amines (e.g., Irganox™ 1010), UV absorbers (e.g., carbon black, titanium dioxide, Tinuvin® P from Ciba-Giegy), stabilizers such as carbodiimide, (e.g., Staboxa™1 P from Bayer), Satrastab™ from SATRA (Shoe and Allied Trades Assoc., Kettering, England), adhesion promoters, leveling agents, fillers, extenders, other polymers, activators, curing agents, colorants, pigments, neutralizing agents, thickeners, non-reactive and reactive plasticizers, coalescing agents such as di(propylene glycol) methyl ether (DPM), waxes, slip and release agents, antimicrobial agents, surfactants such as Pluronic™ F68-LF and IGEPAL™ CO630 and silicone surfactants, metals, salts, flame retardant additives, antiozonants, and the like. Additives may also be used as appropriate in order to make articles or to treat other products (such as by impregnation, saturation, spraying, coating, or the like). The dispersions of this invention, typically, have total solids of at least about 20 wt. %, preferably at least about 25 wt. % and more preferably at least about 30 wt. %.

(v) Blends with Other Polymers and Polymer Dispersions

The dispersions of this invention can be combined with commercial polymers and polymer dispersions by methods well known to those skilled in the art. Preferably, these polymers are acrylate polymers or dispersions as described later. Desirably, the polyacrylate phase is present in an amount of from about 10 to about 50 wt. % based on the combined weight of the polyurethane phase and the polyacrylate phase, more desirably from about 10 to about 40 wt. %, more desirably from about 10, 12, or 14 to about 30 wt. %, and preferably from about 12, 13, 14, or 15 to about 25 wt. %. Such polymers and dispersions include those described in WIPO Publication WO 02/02657 A2, U.S. Pat. Nos. 4,920,176, 4,292,420, 6,020,438, 6,017,997 and a review article by D. P. Tate and T. W. Bethea, Encyclopedia of Polymer Science and Engineering, Vol. 2, p. 537, the disclosures of which are incorporated herein by reference.

Similarly, the dispersions of this invention can be formed by dispersing the prepolymer mixture in a previously formed aqueous dispersion of another polymer or polymers and/or nanoparticles. In other words, the aqueous medium into which the prepolymer mixture is dispersed in accordance with the present invention, can itself be a previously formed aqueous dispersion of another polymer or polymers, including those made by emulsion and suspension polymerization techniques and/or nanoparticles.

(vi) Hybrids with Other Polymers

The aqueous dispersions of this invention can also be used as seed polymers for forming hybrids of polyurethanes with other polymers. This can be done by forming the aqueous dispersions of polyurethane, in the manner described above, and then polymerizing additional monomers by emulsion or suspension polymerization in the presence of these dispersions, i.e., with the inventive dispersions being mixed with the additional monomers before polymerization is completed. Hybrids of polyurethanes and acrylics can be made to advantage by this approach.

Still another way of making hybrid polymers, in accordance with the present invention, is to include ethylenically unsaturated monomers in the polyurethane prepolymer reaction system and to cause these monomers to polymerize when or after the prepolymer is dispersed in aqueous medium. In this approach, the ethylenically unsaturated monomers act as a diluent during prepolymer formation. In the aqueous medium, these ethylenically unsaturated monomers can be polymerized to completion with or without additional monomers being added. Hybrids of polyurethanes and acrylics can be made to advantage by this approach, as well.

In many cases, when making the acrylate portion of the invention, it is advantageous to utilize both an alkyl acrylate monomer and/or an alkyl methacrylate monomer in making the copolymers of this invention. These monomers can include alkyl acrylates, alkyl methacrylates, and alkyl ethacrylates. The alkyl group may contain from 1 to 15 carbon atoms and more desirably from 1 to 10 carbon atoms. Desirable acrylates include n-butyl acrylate, n-butyl methacrylate, ethylhexyl acrylate, ethyl acrylate, ethyl methacrylate, methyl acrylate, and methyl methacrylate. The use of (meth) or (eth) or (meth or eth) indicates (through out this specification) that the item in parentheses is optionally present.

Desirably, the composition of the soft acrylate copolymer is adjusted so that the Tg (glass transition temperature) is below −30, more desirably below −40° C., and preferably from about −40 to about −90° C.

Examples of ethylenically unsaturated monomers that can be used in the process of the invention include mono vinyl aromatic monomers, alpha-beta ethylenically-unsaturated carboxylic acid ester monomers, unsaturated monomers with carboxylic acid groups, vinyl ester monomers, and various combinations of these. The acrylate monomers are, preferably, selected from the group consisting of esters of acrylic and methacrylic acid (e.g., those with 4 to 30 carbon atoms) such as n-butyl(meth)acrylate, methyl(meth)acrylate, ethyl (meth)acrylate, 2-ethylhexyl-(meth)acrylate, cycloalkyl (meth)acrylates, such as isobornyl(meth)acrylate and cyclohexyl(meth)acrylate. Choices among the acrylate monomers are, typically, made to achieve the desired glass transition temperatures (Tg) for the soft copolymers. Methyl methacrylate is a known higher Tg acrylate. Acrylic and methacrylic acid have fairly high Tg values. The vinyl aromatic based monomers include styrene, i.e., styrene or substituted styrenes, for instance alpha-methyl styrene or t-butylstyrene; and vinyltoluene. The diene monomers include dienes such as 1,3-butadiene or isoprene, and mixtures thereof. The ethylenically unsaturated monomers can include vinyl esters with 4 to 25 carbon atoms, such as vinyl acetate, vinyl alkanoate or their derivatives or mixtures thereof can be used in the monomer composition. Nitriles, such as (meth)acrylonitrile, or olefinically unsaturated halides, such as vinyl chloride, vinylidene chloride, and vinyl fluoride can also be used. Preferred vinyl ester monomers include vinyl esters of versatic acids, such as the monomers commercialized by Hexion Specialty Chemicals under the trade names VEOVA® 9, 10 and 11.

Unsaturated monomers with acid (e.g., carboxylic acid) functionality, which include monomers of which the acid groups are latent as, for example, in maleic anhydride, are suitably selected from, but not limited to: acrylic acid, methacrylic acid, oligomerized acrylic acids such as beta-carboxyethyl acrylate or its higher analogues (commercially available from Rhodia as Sipomer™ B-CEA), itaconic acid, fumaric acid, maleic acid, citraconic acid, or the anhydrides thereof. Other acid type monomers include styrene p-sulfonic acid, ethylmethacrylate-2-sulfonic acid and 2-acrylamido-2-methylpropane sulfonic acid. An acid bearing monomer could be polymerized as the free acid or as a salt, e.g., the ammonium or alkali metal salts.

Other monomers that may be present in amounts up to 5, 10, 15, or 20 weight percent, based on the total monomers in the polymers of the polymerization, include acrylonitriles, vinyl chlorides, vinylidene chlorides, and amide functional monomers. Amide-functional comonomers include, but are not limited to, acrylamide and methacrylamide.

Another group of monomers, which are useful in preparing the copolymers of the present invention, are polar non-ionic monomers, such as, hydroxyalkyl(meth)acrylates, (meth) acrylamides and substituted (meth)acrylamides (e.g., N-methyl acrylamide), N-vinyl-2-pyrrolidone, N-vinyl caprolactam, 2-hydroxyethyl(meth)acrylate, 2-hydroxypropyl(meth) acrylate, 4-hydroxybutyl (meth)acrylate, (4-hydroxymethylcyclohexyl)-methyl(meth)acrylate, 1-(2-((2-hydroxy-3-(2-propenyloxy)propyl)amino)ethyl)-2-imidazolidinone, N-methylol (meth)acrylamide, Sipomer® WAM, WAM II (from Rhodia) and other urido-containing monomers, dimethylaminoethyl(meth)acrylate, and dimethylaminopropyl(meth)acrylamide. Mixtures of polar monomers also may be used. Those hydrophilic monomers should be used at appropriate levels, which do not impair the earlier water resistance.

Vinyl aromatic monomers can also be employed as the copolymerizable monomer. However, the total amount of vinyl aromatic monomers utilized in one embodiment for food contact for making the copolymer of this invention will, typically, not exceed about 50 weight percent and in another embodiment not to exceed 33 weight percent of the total weight of monomers employed in making the copolymer (total polymers in polymerization).

Tg values, used herein, are those calculated by using the Fox equation; see T. G. Fox, Bull. Am. Physics Soc., Volume 1, Issue No. 3, page 123, (1956). The formula for calculating the Tg of a copolymer of monomers M1 and M2 is $1/Tg(calc.) = w(M1)/Tg(M1) + w(M2)/Tg(M2)$, wherein Tg(calc.) is the glass transition temperature calculated for the copolymer, w(M1) is the weight fraction of monomer M1 in the copolymer, w(M2) is the weight fraction of monomer M2 in the copolymer, Tg(M1) is the glass transition temperature of the homopolymer of M1, and Tg(M2) is the glass transition temperature of the homopolymer of M2, with all temperatures being in ° K. Glass transition temperatures of homopolymers may be found, for example, in J. Brandrup and E. H. Immergut, ed., Polymer Handbook, Interscience Publishers.

In one embodiment, it is desirable to include non-formaldehyde generating crosslinking monomers in the acrylate copolymer. Crosslinking monomers are present in the structure of the soft acrylate copolymer in an amount from 0.1 or 0.15 to 3, preferably 0.3 or 0.5 to 2 percent by weight based on the weight of the soft acrylate copolymer. The crosslinking is chosen just high enough so that the extensibility of the copolymer film is only slightly decreased in comparison with that of a corresponding non-crosslinked soft acrylate copolymer. In a particular case, the degree of crosslinking is directed toward a particular use. For this purpose, a low content of crosslinking monomer is sufficient.

In one embodiment, the crosslinking monomers have at least two ethylenically unsaturated, free radically polymerizable groups, suitable groups such as allyl, acryl, or methacryl groups, in the molecule. Compounds having at least three such groups, which may be the same or different, may be used. Examples of crosslinking monomers are diol and polyolesters of acrylic acid and/or of methacrylic acid reacted with di- or poly-functional alcohols, such as ethylene glycol diacrylate and dimethacrylate, butylene glycol diacrylate and di methacrylate, dipropylene glycol dimethacrylate, propylene glycol dimethacrylate, pentaerythritol tri- or tetra-acrylate and methacrylate, trimethylolpropane triacrylate and trimethacrylate, and allyl acrylate and methacrylate, divinylbenzene and trivinylbenzene, as well as triallyl cyanurate and triallyl isocyanurate. In many cases, graft crosslinking monomers which contain at least two ethylenically unsaturated, free radically polymerizable groups, among which is at least one allyl group, may be used.

Conventional emulsifiers can be used to form the emulsion of monomers and to stabilize the growing latex particles. Typical anionic emulsifiers include alkali or ammonium alkyl sulfates, alkyl sulfonates, salts of fatty acids, esters of sulfosuccinic acid salts, alkyl diphenylether disulfonates, and the like, and mixtures thereof. Typical nonionic emulsifiers include polyethers, e.g., ethylene oxide and propylene oxide condensates, including straight and branched chain alkyl and alkylaryl polyethylene glycol and polypropylene glycol ethers and thioethers, alkyl phenoxypoly(ethyleneoxy)ethanols having alkyl groups containing from about 7 to about 18 carbon atoms and having from about 4 to about 100 ethyleneoxy units, and polyoxy-alkylene derivatives of hexitol, including sorbitans, sorbides, mannitans, and mannides; and the like, and mixtures thereof. Preferred surfactants include Dextrol™ OC-60, sodium lauryl sulfate, Dowfax™ 2A1, Aerosol™ OT, and dodecylbenzene sulfonate.

The emulsion polymerization employed in synthesizing the copolymer(s) of this invention is carried out in a conventional manner using well-known additives and ingredients, such as emulsifiers, free radical polymerization initiators, and the like, and mixtures thereof. Either thermal or redox initiation processes may be used. The reaction temperature, typically, is maintained at a temperature lower than about 100° C. throughout the course of the reaction. In one embodiment, a reaction temperature between about 25° C. and 95° C. is used.

For the purpose of adjusting pH at the outset of the polymerization, pH control agents and buffers typically are added. The initial reactor pH will normally be within the range of about 3 to about 10. However, other pH values may be obtained in particular applications using pH control agents and buffers well known to those skilled in the art. Non-limiting examples of suitable pH control agents include but are not limited to ammonium and alkali metal hydroxides (such as sodium hydroxide and potassium hydroxide), and mixtures thereof, and the like. Non-limiting examples of suitable buffers include ammonium carbonate, sodium carbonate, sodium bicarbonate, and mixtures thereof, and the like. pH may be adjusted if desired at the end of the polymerization process according to the desired application.

The copolymers, typically, are prepared in the presence of water-soluble or organic solvent-soluble initiators (such as persulfates, peroxides, hydroperoxides, percarbonates, peracetates, perbenzoates, azo-functional compounds) and other free-radical generating species, and mixtures thereof, as is well known to those skilled in the art.

Pigments may be added to adhesive formulations to impart color. Titanium dioxide is an example of a widely used pigment which imparts hiding and a white color. Mineral pigments (such as oxides of iron and chromium), organic pigments (such as phthalocyanine) and active anticorrosive pigments (such as zinc phosphate) are representative examples of other widely used pigments. Some representative examples of widely utilized fillers include chalks, clays, micas, barites, talcs, and silica.

(vii) Water-Borne Energy Curable Polyurethane Compositions

It is already known that water-borne polyurethane and hybrid compositions that can be cured by application of energy (UV and IR radiation and/or electron beams) can be made by end-capping the polyurethane with (meth)acrylic esters and other ethylenically unsaturated monomers. This technology can be applied to this invention to provide energy-curable water-borne polyurethane coatings.

(viii) Alternative Applications

The aqueous polyurethane dispersions of this invention, both in prepolymer and chain extended form, can be used to make coatings and films for porous and non-porous substrates such as papers, non-woven materials, textiles, leather, wood, concrete, masonry, metals, house wrap and other building materials, fiberglass, polymeric articles, personal protective equipment (such as hazardous material protective apparel, including face masks, medical drapes and gowns, and firemen's turnout gear), and the like. Applications include papers and other non-wovens, fibrous materials, films, sheets, composites, and other articles, inks and printing binders, flock and other adhesives, and personal care products such as skin care, hair care, and nail care products, livestock and seed applications, and the like.

Any fibrous material can be coated, impregnated or otherwise treated with the compositions of this invention by methods well known to those skilled in the art, including carpets as well as textiles used in clothing, upholstery, tents, awnings, air bags, and the like. Suitable textiles include fabrics, yarns, and blends, whether woven, non-woven, or knitted, and whether natural, synthetic, or regenerated. Examples of suitable textiles include cellulose acetate, acrylics, wool, cotton, jute, linen, polyesters, polyamides, regenerated cellulose (Rayon), and the like.

Compositions of this invention can also be used to produce articles made of stand-alone films and objects such as personal protective equipment. Examples of protective items include gloves and condoms.

This invention is illustrated by the following examples that are merely for the purpose of illustration and are not to be regarded as limiting the scope of the invention or the manner in which it can be practiced. Unless specifically indicated otherwise, parts and percentages are given by weight.

Polyurethane Dispersion Examples

Unless otherwise noted, the basic procedure used to produce some of the inventive example polymers is as follows:

The polyol(s) is charged to a reactor. The agitation is turned on, and the isocyanate(s) is charged to the reactor. This first stage of the reaction is run at about 180-210° F. (82-99° C.). The end of the reaction is determined by % NCO (isocyanate) titration, and is considered complete when this number is at or below the calculated theoretical % NCO value. Theoretical % NCO means the calculated percent assuming quantitative reaction of all NCO and NCO reactive species. A nitrogen purge is kept on throughout the first stage of the reaction.

The reactor is then cooled to about 140-160° F. (60-71° C.), and methyl ethyl ketone (MEK) is charged, followed by the dihydroxy acid [dimethylol butanoic acid (DMBA) or dimethylol propionic acid (DMPA)]. The reaction is again run to completion, determined by the % NCO titration, and is considered complete when this number is at or below the calculated theoretical value. This portion of the process is hereafter referred to as the "first stage" of the reaction, and the reaction product is referred to as the "prepolymer".

The prepolymer is transferred to a second reactor that contains a specified amount of acetone and/or MEK, and the mixture is cooled to below 105° F. (40.6° C.). Triethylamine (TEA) is charged to the mixture and thoroughly stirred. A specified amount of water at a temperature of about 50-70° F. (10-21° C.) is added over about 5 minutes, under good agitation, and the result is an opaque to "milky" dispersion. A diamine chain extender is then charged to this dispersion over the course of about 5-20 minutes, until the NCO peak generated from an infrared spectrum indicates that the level of NCO remaining is very low. This portion of the process is hereafter referred to as the "second stage" of the reaction, and the reaction product is referred to as the "fully reacted dispersion".

POLYURETHANE EXAMPLES

Example 1

Urethane Prepolymer Dispersion 491 grams of poly THF diol (OH#=38.6) was charged to a reactor. Under agitation, 57 grams of TDI (80/20 isomer mixture of 2,4 and 2,6 toluene diisocyanate) was added. The mixture was heated to a maximum of 180° F. (83° C.), and 0.02 grams of T-9 (tin octoate) catalyst was added to facilitate the reaction. When the theoretical NCO was reached, 140 grams of MEK and 12.3 grams of DMBA was added, and held at a maximum temperature of 166° F. (74° C.) until theoretical NCO was reached. The prepolymer was neutralized with 9 grams of TEA, and 609 grams of this prepolymer was transferred to a reactor containing 440 grams of acetone and 200 grams of MEK. 2.5 grams of Pluronic™ F68-LF surfactant was then added to this prepolymer solution, which was at 102° F. (39° C.). 881 grams of water at 56° F. (14° C.) was added over 4 minutes with good agitation, to form a dispersion. This dispersion was split in ½. To ½ of the dispersion just described, 2.5 grams of a 25% solution in water of 2-methyl pentane diamine (Dytek A) was added. The solvents were then distilled off using a rotary evaporator, producing a fully reacted dispersion with very low residual co-solvent levels.

Additional versions of Example 1 were prepared using a solvent that was 90 wt. % MEK and 10 wt. % isopropanol (instead of the 340 grams of MEK and 440 grams of acetone used above) and a comparable Example 1b was prepared. The isopropanol was added last after the prepolymer had cooled significantly, to minimize reaction with remaining isocyanate. That illustrates that solvents or solvent blends other than MEK/acetone are effective in the process.

Example 2

Urethane Prepolymer Dispersion 558 grams of poly THF diol (OH#=38.6) was charged to a reactor. Under agitation, 67 grams of TDI was added. The mixture was heated to a maximum of 181° F. (83° C.), and held until the theoretical NCO was reached. Next, 160 grams of MEK, 15 grams of DMBA, and 0.02 grams of T-9 catalyst was added. The prepolymer was held at a maximum of 170° F. (77° C.) until theoretical NCO was reached. The prepolymer was neutralized with 11.4 grams of TEA. 609 grams of neutralized prepolymer was charged to a solution of 200 grams of MEK, 440 grams of acetone, and 2.5 grams of F68-LF surfactant. The temperature of this solution was 95° F. (35° C.). 880 grams of water at 57° F. (14° C.) was charged with good agitation to this solution over about 4 minutes. 10 grams of Dytek A (25% solution in water) was added over the course of 32 minutes. The dispersion had a very small NCO peak at this point. The solvents were then distilled off using a rotary evaporator, producing a fully reacted dispersion with very low co-solvent levels.

Example 3

Urethane Prepolymer Dispersion 1856 grams of poly THF diol (OH#=38.6) was charged to a reactor. Under agitation, 219 grams of TDI was added. The mixture was heated to a maximum of 181° F. (83° C.), and held until the theoretical NCO was reached. Next, 531 grams of MEK, 15 grams of DMBA, and 0.06 grams of T-9 catalyst was added. The prepolymer was held at a maximum of 172° F. (78° C.) until theoretical NCO was reached. The prepolymer was neutralized with 36.5 grams of TEA. 2314 grams of neutralized prepolymer was charged to a solution of 1395 grams of acetone, 640 grams of MEK, and 9 grams of F68-LF surfactant. The temperature of this solution was 94° F. (34° C.). 3221 grams of water at 62° F. (17° C.) was charged with good agitation to this solution over about 3 minutes. 23.3 grams of Dytek A (25% solution in water) was added over the course of 15 minutes. The dispersion had a very small NCO peak at this point. The solvents were then distilled off using a rotary evaporator, producing a fully reacted dispersion with very low co-solvent levels.

Example 4

Example 1+Crosslinker 450 grams of the polymer from Example 1 was blended with 6.8 grams of Carbodilite E-02. A finger mold with a thin film of dried coagulant solution (mentioned above) applied to it was lowered slowly into this blend, according to the above-described procedure, held 10 seconds, then slowly removed. A coagulated film was formed on the mold. After the above-described rinsing procedure, the mold was cured for 10 minutes at 250° F. (121° C.). Once cooled, the film was removed. Tensile properties were run on the following day, according to the above-described procedure.

Example 5

Acrylic Example

To a 3000 ml round-bottom flask (reactor), 445 grams of water, 35 grams of itaconic acid, 25 grams of Abex™ 2525 surfactant, and 12 grams of a 30% solution of sodium lauryl sulfate (SLS) were added. A monomer premix was made by charging 380 grams of water, 25 grams of SLS, 38 grams of acrylamide, 18 grams of ethyl acrylate (EA), 185 grams of n-butyl acrylate (BA), 741 grams of 2-ethylhexyl acrylate (EHA), and 2 grams of trimethylolpropane triacrylate (TMPTA). The reactor contents are heated to 74° C., and a solution of 2.7 grams of sodium persulfate in 19 grams of water is added. After about 3 minutes, the metering of the premix into the reactor is begun. The premix is metered in evenly over the course of about 3 hours. A booster initiator was then added, which is a solution of 21 grams of water, 0.7 grams of sodium persulfate, and 0.5 grams of ammonium carbonate. The temperature was held at about 74° C. for an additional 2 hours, with continued agitation. A redox was then done by adding a solution of 1.9 grams of t-butyl hydroperoxide and 0.33 grams of SLS in 16 grams of water. After 5 minutes of mixing, a solution of 1.6 grams of Bruggolite FF6 and 37 grams of water were added, and allowed to mix for a minimum of 30 minutes. To 583 grams of this fully reacted dispersion, 9 grams of dimethyl ethanolamine (DMEA) was added, to raise the pH to 7+.

Example 6

Polyurethane/Acrylic Blend Example 394 grams of the polymer from Example 1 were blended with 80 grams of Hystretch™ V-60 (an acrylate dispersion in water with appropriate Tg) and 3.6 grams of Cymel 385. A finger mold with a thin film of dried coagulant solution (mentioned above) applied to it was lowered slowly into this blend, according to the above-described procedure, held 10 seconds, then slowly removed. A coagulated film was formed on the mold. After the above-described rinsing procedure, the mold was cured for 10 minutes at 300° F. (149° C.). Once cooled, the film was removed. Tensile properties were run on the following day, according to the above-described procedure.

Example 7

Polyurethane/Acrylic Blend Example 295.2 grams of the polymer from Example 1 were blended with 40 grams of Hystretch V-60, 59 grams of Hystretch V-43 (an acrylate dispersion in water with appropriate Tg available from the Lubrizol Corp.), 79.2 grams of water, and 7.1 grams of Carbodilite E-02. A finger mold with a thin film of dried coagulant solution (mentioned above) applied to it was lowered slowly into this blend, according to the above-described procedure, held 10 seconds, then slowly removed. A coagulated film was formed on the mold. After the above-described rinsing procedure, the mold was cured for 10 minutes at 300° F. (149° C.). Once cooled, the film was removed. Tensile properties were run on the following day, according to the above-described procedure.

Example 8

Polyurethane/Acrylic Blend Example 403 grams of the polymer from Example 2 were blended with 71 grams of the polymer from Example 5 and 6.7 grams of Carbodilite E-02. A finger mold with a thin film of dried coagulant solution (mentioned above) applied to it was lowered slowly into this blend, according to the above-described procedure, held 10 seconds, then slowly removed. A coagulated film was formed on the mold. After the above-described rinsing procedure, the mold was cured for 10 minutes at 300° F. (149° C.). Once cooled, the film was removed. Tensile properties were run on the following day, according to the above-described procedure.

Example 9

Polyurethane/Acrylic Blend Example 338 grams of the polymer from Example 2 were blended with 23 grams of Hystretch V-60 and 23 grams of Hystretch V-43, 111 grams of water, and 2.2 grams of Cymel 385. A finger mold with a thin film of dried coagulant solution (mentioned above) applied to it was lowered slowly into this blend, according to the above-described procedure, held 10 seconds, then slowly removed. A coagulated film was formed on the mold. After the above-described rinsing procedure, the mold was cured for 10 minutes at 300° F. (149° C.). Once cooled, the film was removed. Tensile properties were run on the following day, according to the above-described procedure.

The following Tables 1 and 2 summarize the composition and physical properties of Examples 1-9 in terms of composition and film properties.

TABLE 1

| Ex. | Polyol MW | NCO/OH | Wt. % Polyol | Wt. % DMBA | Isocyanate | Isocyanate wt. % |
|---|---|---|---|---|---|---|
| 1 | 2907 | 1.3/1 | 87.6 | 2.2 | TDI | 10.2 |
| 2 | 2907 | 1.3/1 | 87.2 | 2.4 | TDI | 10.4 |
| 3 | 2907 | 1.3/1 | 87.4 | 2.3 | TDI | 10.3 |

TABLE 2

| | Total Polyol wt. % | COOH wt. % | DMBA wt. % | Iso wt. % | 100% Modulus PSI | 100% Modulus MPa | 500% Modulus PSI | 500% Modulus MPa | Tensile Strength PSI | Tensile Strength MPa | Alcohol resistance |
|---|---|---|---|---|---|---|---|---|---|---|---|
| Ex 1 | 87.6 | 0.67 | 2.2 | 10.2 | 239 | 1.6 | 394 | 2.7 | 3027 | 20.9 | — |
| Ex 4 | 87.6 | 0.67 | 2.2 | 10.2 | 268 | 1.8 | 539 | 3.7 | 3601 | 24.8 | Fair-Good |
| Ex 6 | 87.6 | 0.67 | 2.2 | 10.2 | 254 | 1.8 | 558 | 3.8 | 2510 | 17.3 | V. Good |
| Ex 7 | 87.6 | 0.67 | 2.2 | 10.2 | 241 | 1.7 | 493 | 3.4 | 2576 | 17.8 | V. Good |
| Ex 8 | 87.2 | 0.73 | 2.4 | 10.4 | 196 | 1.4 | 524 | 3.6 | 3044 | 21.0 | V. Good |
| Ex 9 | 87.2 | 0.73 | 2.4 | 10.4 | 273 | 1.9 | 647 | 4.5 | 2890 | 19.9 | V. Good |

Glove Dipping Procedure

A coagulant dispersion/solution was made using the following ingredient ratios:

| | |
|---|---|
| Water | 100.00 parts |
| Natrosol ™ 250HR PA | .27 parts |
| Calcium Nitrate | 20.00 parts |
| Aerosol ™ OT-NV | .20 parts |
| Calcium Carbonate | 8.00 parts |
| DeeFo ™ 97-3 | .05 parts |

The water is the carrier for the coagulant dispersion/solution. The Natrosol 250HR PA (hydroxyethyl cellulose (HEC) a nonionic from Hercules) is used as a thickener and rheology modifier. The calcium nitrate is the active ingredient that induces coagulation of a polymer onto a mold. The Aerosol OT-NV is a surfactant that allows for the coagulant solution to deposit fully and evenly on the mold. The calcium carbonate is used as an agent to help the coagulated and cured polymer release from the mold. The DeeFo 97-3 is used as a defoamer from Munzing to prevent "bubble defects" from being deposited on the mold.

It should be recognized that there are numerous other thickeners, coagulants, surfactants, mold release agents, and defoamers that can be substituted for the above ingredients. Similar properties can likely be obtained using substitute materials.

When in use, the coagulant dispersion/solution is kept under constant mild agitation, to keep the dispersion uniform and well-mixed. This was done using a magnetic stirrer and magnetic stir bar. It should be recognized that there are other methods to accomplish this, but the main goal is to ensure consistency and uniformity of the coagulant dispersion/solution when it is applied to the mold.

For testing purposes, a mold in the shape and style of a finger was used. The mold was first cleaned using warm water, and dried thoroughly with a paper towel. It was then visually inspected for contaminants, and re-cleaned as necessary. The cleaned mold was dipped to approximately 80% of its length into the coagulant dispersion/solution, and allowed to drip dry for about 1 minute, while being held in a vertical position. Warm air was then blown on the mold until all the liquid had been evaporated. After this process, a thin film of the dried coagulant was left on the mold.

The mold was then slowly dipped into the polymer dispersion over about 4 seconds. Once the mold was submerged to just below the level of the coagulant coverage, it was held in that position for 10 seconds. It was then removed from the polymer dispersion steadily over the course of about 4 seconds, and a coagulated film was formed on the surface of the mold. The mold and film were rinsed with DI water for about 30 seconds, and placed in an oven to cure. Two sets of cure conditions were used in the testing. One was 10 minutes at 300° F. (149° C.), and the other was 15 minutes at 250° F. (121° C.). Cure conditions are noted in the data tables appearing later in this document.

It is recognized that there can be many variations in the temperatures and timings of this procedure that can have some influence on the final properties. Unless the variation is severe, few significant changes should be seen. Changes will likely be to the detriment of one or more properties, including but not limited to modulus, strength, resistance, color development, cost, uniformity, etc.

Once cured, the mold and film were run under cold water, until they were close to room temperature. They were blotted dry with a paper towel, and dusted with calcium carbonate to allow for easy removal from the mold without cling. It is recognized that in a manufacturing operation, the preferred style of glove is powder-free, so a donning coating would be applied as part of the process, instead of a powder.

The cured film was then stripped from the mold. It was cut along one side to form a flat, single-layered film. Dumbbell type specimens were punched out from this film. The dimensions are 1½ inches in length, ⅝ inch width at the ends, and 3/16 inch width in the center test area. Tensile properties were run using a ¾ inch gage length, and a 12 inch per minute test speed. The reported modulus values are typically an average of 5 samples. Reported tensile strength and elongation are typically an average of four or five samples.

Alcohol resistance testing was performed in the following manner. Films which were prepared by the above-described method were stretched side-by-side by hand to about 300% elongation. A drop of alcohol solution was placed on the stretched polymers and allowed to sit until either the film broke or all the fluid had evaporated. A relative subjective rating was given to the films. A control polyisoprene sample of known resistance was used for comparison in each test. A rating of 'very good' was assigned if the film performed nearly as well as polyisoprene. A rating of 'good' was assigned if the film became sticky, but did not break. A rating of 'fair-good' was assigned if the film broke within approximately 20 seconds. A rating of 'fair' was assigned if the film broke within approximately 5-10 seconds. A rating of 'poor' was assigned if the film broke in less than 5 seconds.

While certain representative embodiments and details have been shown for the purpose of illustrating the subject invention, it will be apparent, to those skilled in this art, that various changes and modifications can be made therein without departing from the scope of the subject invention.

What is claimed is:

1. A waterborne urethane polymer dispersion comprising:
   a) an aqueous continuous phase being at least 25 wt. % water;
   b) a dispersed polyurethane phase(s) with an acid number less than 12.6 mg KOH/gram,
   wherein said polyurethane phase(s) comprises a reaction product(s) of
   b1) about 20 wt. % or less comprising reactants characterized as a polyisocyanate(s), wherein at least 80 wt. % of said polyisocyanates are aromatic diisocyanates, and
   b2) about 80 wt. % or more of one or more reactants characterized as multi-functional isocyanate-reactive compounds, wherein at least 80 wt. % of said multi-functional isocyanate-reactive compounds
     i) are above 2000 number average molecular weight,
     ii) are selected from the group consisting of polyethers of 3 to 5 carbon atoms per repeat unit, polycarbonates, polydienes, and mixtures thereof, and
     iii) have a functionality when reacting with isocyanates of about 1.95 to about 2.05;
   c) optionally a polyacrylate phase existing primarily within the dispersed polyurethane phase and/or separately dispersed in the aqueous continuous phase, wherein said polyacrylate is characterized by having an estimated glass transition temperature of less than minus 10° C.; and
   d) a crosslinker for the polyurethane phase and/or the polyacrylate phase in an amount from about 0.5 to about 5 wt. % based on the solids of the combined polyacrylate phase and polyurethane phase.

2. The waterborne polymer dispersion of claim 1, wherein said polyacrylate phase is present in an amount of from about 10 to about 50 wt. % based on the combined weight of the polyurethane phase and polyacrylate phase.

3. The waterborne polymer dispersion of claim1, wherein present said acid number is less than 8.8 mg KOH/gram.

4. The waterborne polymer dispersion of claim 1, wherein at least 80 wt. % of said polyurethane phase is derived from multi-functional isocyanate-reactive compounds characterized as
   i) above 2000 number average molecular weight,
   ii) selected from the group consisting of hydroxyl terminated polytetrahydrofuran, hydroxyl terminated polycarbonates, and mixtures thereof, and
   iii) having a functionality of about 1.95 to 2.05 when reacting with isocyanates.

5. A waterborne polymer dispersion according to claim 1, wherein the polyacrylate is present from about 10 to about 50 wt. % based on the combined weight of said polyurethane phase and said polyacrylate phase; and wherein said polyacrylate phase is characterized as having an estimated glass transition temperature of less than minus 40° C.

6. A waterborne polymer dispersion according to claim 5, wherein said polyurethane phase and said polyacrylate phase co-exist in a hybrid particle phase.

7. A dipped article or cured film comprising a dried film from the waterborne polymer dispersion of claim 1 having a modulus at 100% elongation of less than 290 psi (2.0 MPa), a modulus at 500% elongation of less than 700 psi (4.8 MPa) and a tensile strength of greater than 2500 psi (17.2 MPa).

8. The dipped article or cured film according to claim 7, cured with a formaldehyde free crosslinking agent.

9. A process for forming a dipped article comprising:
   forming a waterborne polyurethane dispersion according to claim 1, dipping a form of appropriate shape into said waterborne polyurethane dispersion forming a film thereon, evaporating the water phase from said film, optionally heating said film to further dry and/or crosslink said film.

10. A process according to claim 9 wherein said waterborne polyurethane dispersion according to claim 1 is prepared by the acetone/MEK process.

11. A process according to claim 9, wherein said form is coated with a calcium salt dipping solution prior to dipping said form into said waterborne polyurethane dispersion.

12. A process according to claim 9, wherein said film is cured by a formaldehyde free crosslinker.

13. A process according to claim 9, wherein said film is cured with a carbodiimide crosslinker.

14. A process according to claim 9, wherein said waterborne polyurethane dispersion contains an aminic chain extender.

15. A process according to claim 9, wherein said form is in the shape of a surgeon's glove.

16. A process according to claim 9, wherein said film has physical properties of a modulus at 100% elongation of less than 290 psi (2.0 MPa), a modulus at 500% elongation of less than 700 psi (4.8 MPa) and a tensile strength of greater than 2500 psi (17.2 MPa).

17. A waterborne polymer dispersion according to claim 1, wherein said polyurethane further comprises the residue from an aminic chain extender and/or water chain extension.

18. A waterborne polymer dispersion according to claim 1, wherein said acid number less than 12.6 mg KOH/gram in said dispersed polyurethane phase(s) is derived from dimethylolpropanoic acid (DMPA) and/or dimethylol butanoic acid (DMBA).

19. A waterborne polymer dispersion according to claim 1, wherein said acid number less than 12.6 mg KOH/gram in said dispersed polyurethane phase(s) is derived from dimethylol butanoic acid (DMBA).

* * * * *